United States Patent
Lazic

(10) Patent No.: US 10,863,990 B2
(45) Date of Patent: Dec. 15, 2020

(54) MALLEABLE PLASTIC SURGICAL CLIP

(71) Applicant: Lazic Besitz GmbH & Co. KG, Tuttlingen (DE)

(72) Inventor: Daniel Lazic, Tuttlingen (DE)

(73) Assignee: LAZIC BESITZ GMBH & CO KG, Tuttlingen (DE)

( * ) Notice: Subject to any disclaimer, the term of this patent is extended or adjusted under 35 U.S.C. 154(b) by 172 days.

(21) Appl. No.: 16/138,972

(22) Filed: Sep. 22, 2018

(65) Prior Publication Data
US 2019/0090878 A1 Mar. 28, 2019

(30) Foreign Application Priority Data

Sep. 25, 2017 (EP) ..................... 17192869

(51) Int. Cl.
| | |
|---|---|
| A61B 17/122 | (2006.01) |
| A61B 17/02 | (2006.01) |
| A61B 17/00 | (2006.01) |

(52) U.S. Cl.
CPC ........ *A61B 17/122* (2013.01); *A61B 17/1222* (2013.01); *A61B 2017/00477* (2013.01); *A61B 2017/00526* (2013.01); *A61B 2017/00862* (2013.01); *A61B 2017/0287* (2013.01)

(58) Field of Classification Search
CPC . A61B 17/122; A61B 17/128; A61B 17/1222; A61B 17/064; A61B 17/068; A61B 2017/00477; A61B 2090/037; Y10T 24/398; Y10T 24/344; Y10T 24/44872; Y10T 24/44906; Y10T 24/44274

USPC ......................................................... 606/158
See application file for complete search history.

(56) References Cited

U.S. PATENT DOCUMENTS

| | | | | |
|---|---|---|---|---|
| 3,616,497 A | * | 11/1971 | Esposito | ............... H01L 23/291 24/542 |
| 4,524,992 A | * | 6/1985 | Linn | ......................... B42F 9/00 24/487 |
| 4,586,503 A | | 5/1986 | Kirsch et al. | |

(Continued)

FOREIGN PATENT DOCUMENTS

| | | |
|---|---|---|
| DE | 34 43 367 A1 | 6/1985 |
| DE | 19520158 A1 | 12/1996 |

(Continued)

*Primary Examiner* — Katrina M Stransky
*Assistant Examiner* — Raihan R Khandker
(74) *Attorney, Agent, or Firm* — Hackler Daghighian Martino & Novak

(57) ABSTRACT

An integral surgical clip includes two clamping arms and a non-spring-elastic connection portion that interconnects the two clamping arms in an integral manner. The two clamping arms on account of a plastic deformation of the clip are pivotable towards one another from an opened initial position up to a closed end position. The two clamping arms engage on the connection portion so as to be mutually spaced apart and are in each case extended beyond the connection portion by one lever arm molded thereon, and wherein, by squeezing the two lever arms, the two clamping arms, on account of a plastic deformation of the connection portion, are pivotable from the closed end position to an opened position. The two lever arms, in particular at the external ends thereof, are interconnected by an external connection arm.

18 Claims, 3 Drawing Sheets

(56) References Cited

U.S. PATENT DOCUMENTS

| | | | | |
|---|---|---|---|---|
| 4,671,281 | A | * | 6/1987 | Beroff .................. A61B 17/122 |
| | | | | 606/111 |
| 6,071,290 | A | | 6/2000 | Compton |
| 8,403,956 | B1 | * | 3/2013 | Thompson ......... A61B 17/1222 |
| | | | | 606/219 |
| 8,795,302 | B2 | * | 8/2014 | Wild .................. A61B 17/1227 |
| | | | | 606/157 |
| 2009/0254090 | A1 | * | 10/2009 | Lizee ................ A61B 17/0642 |
| | | | | 606/75 |
| 2012/0184976 | A1 | | 7/2012 | Nakamura |
| 2012/0228355 | A1 | * | 9/2012 | Combrowski ..... A61B 17/1285 |
| | | | | 227/175.1 |
| 2014/0114332 | A1 | | 4/2014 | Lutze |

FOREIGN PATENT DOCUMENTS

| | | |
|---|---|---|
| DE | 10 2011 001 798 A1 | 10/2012 |
| WO | 97 11645 A1 | 4/1997 |

* cited by examiner

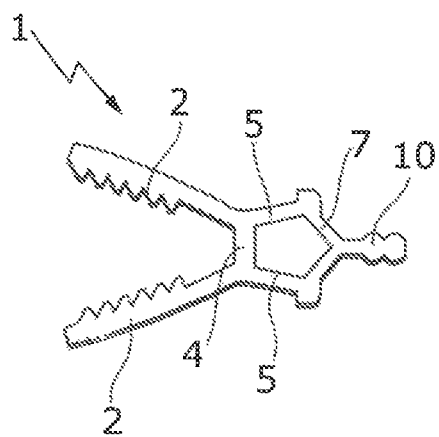
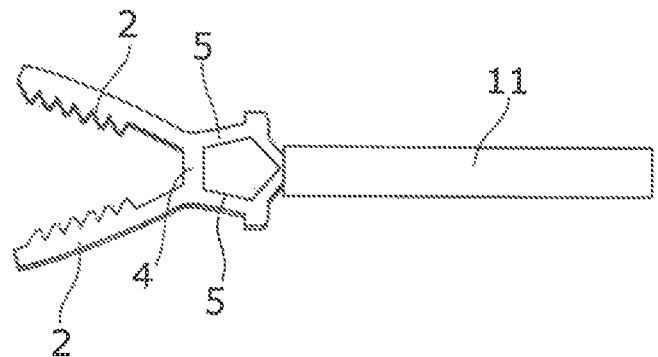
Fig. 3a                Fig. 3b
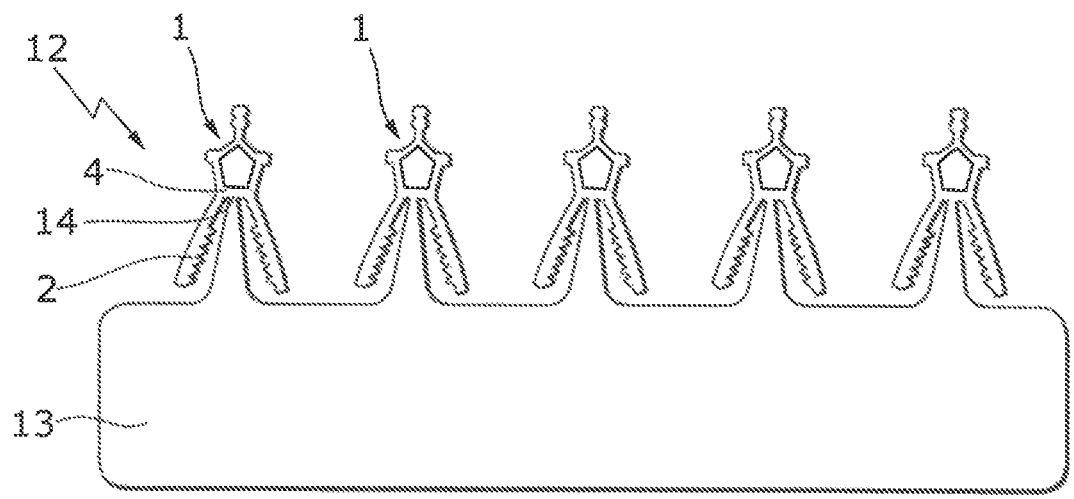
Fig. 4

MALLEABLE PLASTIC SURGICAL CLIP

CROSS-REFERENCE TO RELATED APPLICATIONS

This application claims priority to European Patent Application No. 17 192 869.0 filed Sep. 25, 2017, the entire contents of which are hereby incorporated by this reference.

FIELD OF THE INVENTION

The invention relates to an integral surgical clip, in particular made from metal, comprising two clamping arms and a non-spring-elastic connection portion that interconnects the two clamping arms in an integral manner, wherein the two clamping arms on account of a plastic deformation of the clip are pivotable towards one another from an opened initial position up to a closed end position, wherein the two clamping arms engage on the connection portion so as to be mutually spaced apart and are in each case extended beyond the connection portion by one lever arm molded thereon, and wherein, by squeezing the two lever arms, the two clamping arms, on account of a plastic deformation of the connection portion, are pivotable from the closed end position to an opened position.

BACKGROUND OF THE INVENTION

A surgical clip of this type has become known, for example, by way of DE 34 43 367 A1.

Such surgical clips generally serve for closing off vessels by pinching.

Further, a surgical clip known from DE 195 20 158 A1 is made from metal, and is U-shaped or V-shaped, comprising two clamping arms and a connection part that interconnects said two clamping arms in an integral manner, said connection part having the function of a plastically deformable hinge. The two clamping arms on the internal side of the clip have mutually facing profiled clamping faces which in a plastic deformation of the connection portion are capable of being compressed against one another in a permanently clamping manner. The clip, by squeezing the two clamping arms, is closed in a force-fitting manner and cannot be reopened.

SUMMARY OF THE INVENTION

By contrast, the present invention has the object of stabilizing the two clip halves when the clamping arms and lever arms are being squeezed.

This object is achieved according to the invention in that the two lever arms, in particular at the external ends thereof, are interconnected by an external connection arm. The surgical clip is preferably a laser-cut blank from metal or else a plastics material, in which the connection portion can be plastically deformed at least twice.

The two clamping arms, on account of a plastic deformation of the connection portion, or the transition between the clamping arm and the connection portion, or a combination thereof, are pivotable towards one another from the opened initial position up to the closed end position.

In order for a predetermined kinking point to be configured, the connection portion has a smaller cross-sectional area than the clamping arms and/or lever arms, thus, for example in the case of an identical thickness, a smaller width than the clamping arms and/or lever arms.

The external angle that is in each case enclosed by the clamping arms and the lever arms is particularly preferably between 100° and 170°, preferably between 120° and 150°, and the internal angle that is in each case enclosed by the clamping arms and the connection portion in the initial position is particularly preferably between 100° and 170°, preferably between 120° and 150°.

The two lever arms on the external sides thereof that face away from one another preferably have in each case one protrusion in order that the clip can be gripped in a defined manner by a forceps.

In order for a predetermined kinking point to be configured, the external connection portion preferably has a smaller cross-sectional area than the clamping arms and/or lever arms, thus, for example in the case of an identical thickness, a smaller width than the clamping arms and/or lever arms. The external connection arm in the initial position is advantageously angled outwards, in particular in a V-shaped manner, so as to form a predetermined kinking point when the lever arms are squeezed.

The external connection arm preferably has a projecting extension to which a thread or tape can be attached or onto which a (silicone) tube can be plugged so as to hold tissue, for example in order for the meninx to be stretched out of the way when carrying out surgery.

The invention also relates to a clip holder, in particular from metal, comprising a holding plate and at least one surgical clip, preferably a plurality of surgical clips, designed as above, that is/are in each case connected to the holding plate in an integral manner by way of at least one predetermined breaking point. In order for costs to be saved, the clips are made conjointly with the holding plate from a metal sheet, in particular laser-cut from the latter. The clip holder simultaneously forms an operating part which can be readily held in the hand and from which a clip can be twisted off by means of a pair of pliers. The predetermined breaking point in constructive terms is thinner than the clip such that the clip remains dimensionally stable when being twisted off.

The predetermined breaking point is preferably disposed on the internal side of the connection portion that faces the clamping arms, since a sharp break-off point does not interfere here and the risk of injury is thus very minor.

Further advantages and advantageous embodiments of the subject matter of the invention are derived from the description, the claims, and the drawing. The features mentioned above and yet to be set forth can likewise be used individually or in a plurality thereof in arbitrary combinations. The embodiments shown and described are not to be understood as an exhaustive enumeration but rather have an exemplary character in order for the invention to be visualized. In the drawing:

BRIEF DESCRIPTION OF THE DRAWINGS

FIGS. 3a, 3b show the second surgical clip shown in FIG. 2 having an additional extension (FIG. 3a) and having a tube plugged thereonto (FIG. 3b); and FIG. 4 shows a clip holder having a plurality of surgical clips according to the invention molded thereon in an integral manner.

DETAILED DESCRIPTION OF THE PREFERRED EMBODIMENTS

Figure 1A:
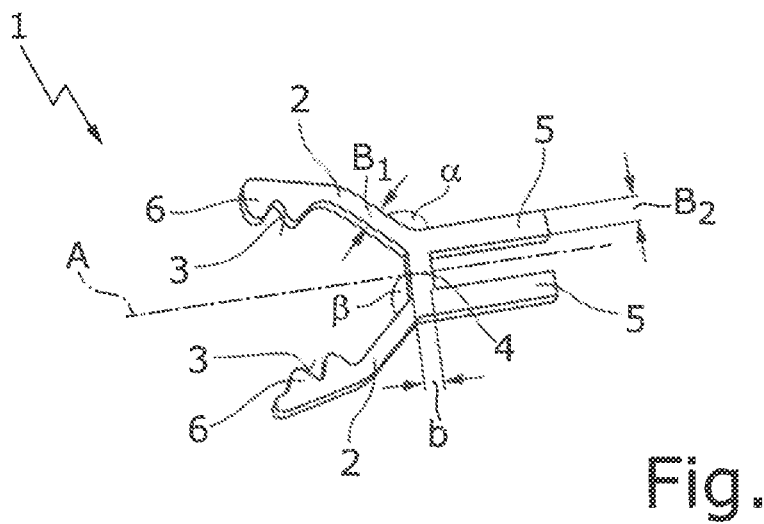
FIGS. 1a-1c show a first surgical clip according to the invention in an opened initial position (FIG. 1a), in a closed end position (FIG. 1b), and in a reopened position (FIG. 1c)

The integral surgical clip 1 shown in FIG. 1a is mirror-symmetrical in terms of the longitudinal central plane A thereof and comprises two kinked clamping arms 2 which on the mutually facing internal sides thereof have clamping faces 3; a non-spring-elastic connection portion 4 which interconnects the two clamping arms 2 in an integral manner and on which the two clamping arms 2 engage so as to be mutually spaced apart; and two lever arms 5 which are molded on the clamping arms 2 in integral manner and which extend the two clamping arms 2 beyond the connection portion 4 and which in the initial position shown in FIG. 1a run so as to be mutually parallel. The clamping arms 2 and lever arms 5 thus form two clip halves which are mutually spaced apart by the connection portion 4.

The clip 1 has a uniform thickness and can be, for example, a laser-cut metal-sheet or plastics material blank. The width b of the connection portion 4 is smaller than the widths B1, B2 of the clamping arms 2 and lever arms 5, such that the connection portion 4 by virtue of the smaller cross-sectional area thereof configures a predetermined kinking point. The external angle α that is in each case enclosed by the clamping arms 2 and the lever arms 5 is approx. 135°, and the internal angle β that is in each case enclosed by the clamping arms 2 and the connection portion 4 in the initial position shown in FIG. 1a is likewise approx. 135°.

Figure 1B:
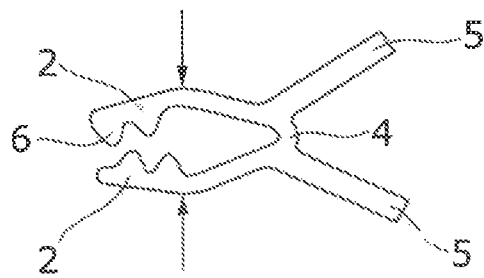

By squeezing the two clamping arms 2 by means of a forceps, such as is indicated by the two arrows in FIG. 1b, the two clamping arms 2, on account of a plastic deformation of the connection portion 4, can be pivoted or bent, respectively, towards one another from the opened initial position up to a closed end position in which teeth 6 of the clamping faces 3 mesh. The connection portion 4 thus has the function of a hinge. When being squeezed, the clamping arm 2 and the lever arm 5 engaging thereon, by virtue of the larger cross-sectional area thereof, are not bent in relation to one another but remain dimensionally stable.

Figure 1C:
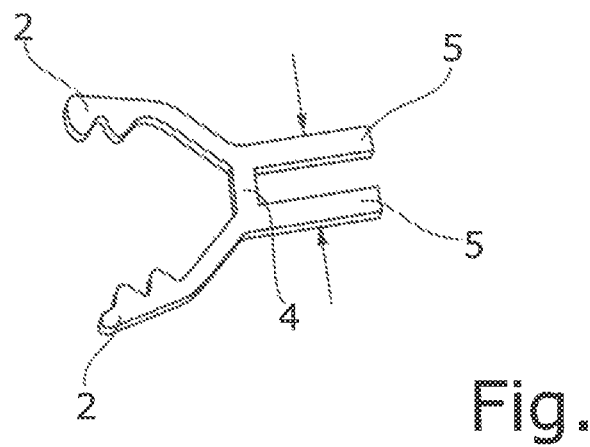

By squeezing the now spreaded two lever arms 5 by means of a forceps, such as is indicated by the two arrows in FIG. 1c, the two clamping arms 2, on account of a plastic deformation of the connection portion 4, can be pivoted or bent, respectively, from the closed end position back to an opened position. When being squeezed, the clamping arm 2 and the lever arm 5 engaging thereon, by virtue of the larger cross-sectional area thereof, are not bent in relation to one another but remain dimensionally stable.

Figure 2A:
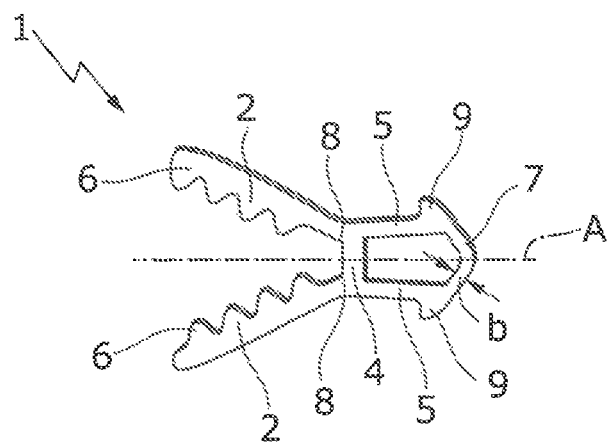
FIGS. 2a-2c show a second surgical clip according to the invention in the opened initial position (FIG. 2a), in a closed end position (FIG. 2b), and in a reopened position (FIG. 2c)

The clip 1 shown in FIG. 2a differs from the clip of FIG. 1 substantially in that the two lever arms 5 here at the external ends thereof are interconnected by an external connection arm 7 which has a smaller cross-sectional area than the clamping arms 2 and lever arms 5. The external connection arm 7 is angled outwards in a V-shaped manner and has the same thickness but a smaller width b than the width of the clamping arms 2 and lever arms 5, so as to configure a predetermined kinking point. The clamping arms 2 are embodied curved instead of angled as in FIG. 1.

Figure 2B:
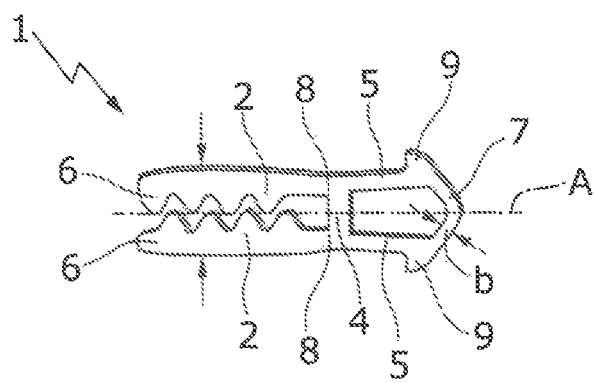

By squeezing the two clamping arms 2 by means of a forceps, as is indicated in FIG. 2b by the two arrows, the two clamping arms 2 in each case, on account of a plastic deformation of the transition 8 between the clamping arm 2 and the connection portion 4, can be pivoted or bent, respectively, towards one another from the opened initial position up to a closed end position in which the teeth 6 of the clamping faces 3 mesh. The transition 8 in the closing movement thus has the function of a hinge. When the clamping arms 2 are being squeezed, the connection portion 4 and the lever arms 5 by virtue of the external connection arm 7 are not plastically deformed but remain dimensionally stable.

Figure 2C:
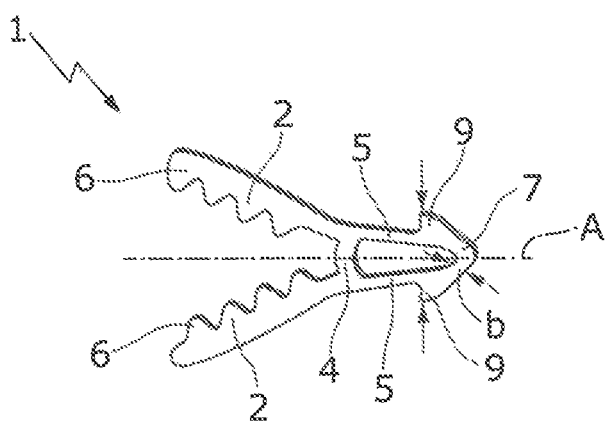

By squeezing the two lever arms 5 by means of a forceps, as is indicated in FIG. 2c by the two arrows, the two clamping arms 2, on account of a plastic deformation of the connection portion 4, can be pivoted or bent, respectively, from the closed end position back to an opened position. When being squeezed, the clamping arm 2 and the lever arm 5 engaging thereon, by virtue of the larger cross-sectional area thereof, are not bent in relation to one another but remain dimensionally stable. When the lever arms 5 are being squeezed, the external connection arm 7 is also plastically deformed and prevents that the two clip halves depart from the clip plane. Furthermore, the two lever arms 5 on the ends on the external sides thereof that face apart from one another have in each case one protrusion 9 in order for the clip 1 to be able to be better received in a forceps.

The two clamping arms 2 in the case of the clip 1 of FIG. 1 are pivotable towards one another up to the closed end position on account of a plastic deformation of the connection portion 4, and in the case of the clip 1 of FIG. 2 on account of a plastic deformation of the transition 8, but in the case of clips not shown here can be pivoted to the closed end position also on account of a combined plastic deformation of the connection portion 4 and of the transition 8.

FIG. 3a shows the clip 1 of FIG. 2 having an additional extension 10 which is molded on the external connection arm 7 in an integral manner, more specifically on the tip of the V-shaped external connection arm 7, and projects to the rear. A thread can be attached to the extension 10, or a silicone tube 11 can be plugged thereonto, as is shown in FIG. 3b, so as to be able to hold tissue, for example in order for the meninx to be stretched out of the way when carrying out surgery.

The clip holder 12 shown in FIG. 4 comprises a holding plate 13 and a plurality of clips 1 which are in each case connected to the holding plate 13 in an integral manner by way of a predetermined breaking point 14. The clips 1 conjointly with the holding plate 12 are made from a metal sheet, in particular laser-cut from a metal sheet. The predetermined breaking point 14 is located on the internal side of the connection portion 4 that faces the clamping arms 2, since a sharp break-off point here does not interfere and the risk of injury is very minor. The predetermined breaking point 14 in terms of construction is thinner than the remainder of the clip 1 such that the clip 1 remains dimensionally stable when being twisted off. The clip holder 12 simultaneously forms an operating part which can be readily held in the hand. The operator can grip the two clamping arms 2 of a clip 1 with the other hand by means of a forceps, release the clip 1 from the holding plate 13 by twisting off the predetermined breaking point 14, and then apply the clip 1 directly, without having to change or switch the grip.

What is claimed is:
1. An integral surgical clip, comprising:
two clamping arms and a non-spring-elastic connection portion that interconnects the two clamping arms in an integral manner;

wherein the two clamping arms on account of a plastic deformation of the clip are pivotable towards one another from an opened initial position up to a closed end position;

wherein the two clamping arms engage on the connection portion so as to be mutually spaced apart and are in each case extended beyond the connection portion by one lever arm molded thereon, and wherein, by squeezing the two lever arms, the two clamping arms, on account of a plastic deformation of the connection portion, are pivotable from the closed end position to an opened position;

wherein the two lever arms are interconnected by an external connection arm, wherein the external connection arm is configured to plastically deform by squeezing the two lever arms.

2. The surgical clip according to claim 1, wherein the two clamping arms on account of a plastic deformation of the connection portion are pivotable towards one another from the opened initial position up to the closed end position.

3. The surgical clip according to claim 1, wherein the two clamping arms on account of a plastic deformation of the transition between the clamping arm and the connection portion are in each case pivotable towards one another from the opened initial position up to the closed end position.

4. The surgical clip according to claim 1, wherein the connection portion has a smaller cross-sectional area than the clamping arms and/or lever arms.

5. The surgical clip according to claim 4, wherein the clamping arms and/or lever arms and the connection portion have the same thickness, and the width of the connection portion is smaller than the width of the clamping arms and/or lever arms.

6. The surgical clip according to claim 1, wherein the two lever arms on external sides thereof that face away from one another have in each case one protrusion.

7. The surgical clip according to claim 1, wherein the external connection arm has a smaller cross-sectional area than the clamping arms or lever arms.

8. The surgical clip according to claim 7, wherein the clamping arms and/or lever arms and the external connection arm have the same thickness, and the width of the external connection arm is smaller than the width of the clamping arms and/or lever arms.

9. The surgical clip according to claim 1, wherein the external connection arm at least in the closed end position is angled outwards.

10. The surgical clip according to claim 1, wherein the external connection arm has an outwardly projecting extension.

11. The surgical clip according to claim 1, wherein the surgical clip, with the exception of teeth that are present on the clamping arms is mirror-symmetrical in relation to the longitudinal central plane of said surgical clip.

12. The surgical clip according to claim 1, wherein the surgical clip is a laser-cut blank.

13. The surgical clip according to claim 1, wherein the surgical clip is made from metal.

14. The surgical clip according to claim 1, wherein the two lever arms, at the external ends thereof, are interconnected by the external connection arm.

15. The surgical clip according to claim 9, wherein the external connection arm at least in the closed end position is angled outwards in a V-shaped manner.

16. A clip holder comprising a holding plate and the integral surgical clip of claim 1, or a plurality of the integral surgical clips of claim 1, that is/are in each case connected to the holding plate in an integral manner by way of at least one predetermined breaking point.

17. The clip holder according to claim 16, wherein the predetermined breaking point is disposed on the internal side of the connection portion that faces the clamping arms.

18. The clip holder according to claim 16, wherein the clip holder is made from metal.

\* \* \* \* \*